US000001185H

United States Statutory Invention Registration [19]

[11] Reg. Number: H1185

Henderson et al.

[43] Published: May 4, 1993

[54] PROCESS FOR ABSORPTION OF DIAMONDOIDS FROM NATURAL GAS

[75] Inventors: James K. Henderson, New Orleans; John R. Sitzman, Mandeville, both of La.

[73] Assignee: Exxon Production Research Company, Houston, Tex.

[21] Appl. No.: 862,877

[22] Filed: Apr. 3, 1992

[51] Int. Cl.[5] ..... C07C 7/10

[52] U.S. Cl. ..... 423/245.2; 585/803

[58] Field of Search ..... 585/803; 423/245.1, 423/245.2, 245.3

[56] References Cited

U.S. PATENT DOCUMENTS

| | | | |
|---|---|---|---|
| 4,952,747 | 8/1990 | Alexander et al. | 585/825 |
| 4,952,748 | 8/1990 | Alexander et al. | 585/803 |
| 4,952,749 | 8/1990 | Alexander et al. | 585/803 |
| 4,982,049 | 1/1991 | Alexander et al. | 585/803 |

OTHER PUBLICATIONS

Levenspiel, *Chemical Reaction Engineering: An Introduction to the Design of Chemical Reactors,* John Wiley & Sons Inc., pp. 384–385, 396–399, (1962).

*Primary Examiner*—Edward A. Miller
*Attorney, Agent, or Firm*—Susan A. McLean

[57] ABSTRACT

A process for removing diamondoids from a stream of natural gas. In this process, contact between a solvent liquid and natural gas containing diamondoids occurs in a stepwise counter current cascaded fashion. The stepwise counter-current cascaded arrangement substantially improves the removal of the light diamondoids (adamantane). The contacting (mixing) of the gas and solvent liquid allows the liquid to absorb the diamondoids contained in the gas. The gas and liquid are then separated thereby removing the diamondoids from the gas. In the preferred embodiment, a multi -staged trayed solvent contractor tower is used to facilitate the stepwise counter current cascaded contacting in the gas production process immediately after the separation of the gas from any liquid in the gas. The partially saturated diamondoid liquid solvent from the tower can also be mixed with the gas at a point before the separation of the gas from any reservoir formation liquid in order to enhance the diamondoid removal process.

11 Claims, 3 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

PROCESS FOR ABSORPTION OF DIAMONDOIDS FROM NATURAL GAS

FIELD OF THE INVENTION

This invention relates to the removal of diamondoid components from natural gas streams during gas processing. In particular, it relates to absorbing the diamondoid compounds into a liquid solvent that contacts the natural gas.

BACKGROUND OF THE INVENTION

Certain natural gas streams contain diamondoid compounds. These diamondoid compounds are a family of volatile C10+ hydrocarbons with lattice-like structures. Some of these diamondoids form solids at warmer than ambient (greater than 100° F.) temperatures when they are condensed from natural gas streams. These diamondoids are present in trace quantities in the natural gas reservoirs themselves.

New sources of hydrocarbon gases are now being produced which contain significantly higher concentrations of diamondoids. Whereas in the past the amount of diamondoid compounds has typically been too small to cause operational problems such as plugging of production equipment, these new sources have experienced the problem of plugging the natural gas production equipment. Costly maintenance and repair time is required to remove the diamondoids. These diamondoid solids must be removed from the natural gas stream by appropriate means to maintain satisfactory production operations.

Although recent patents by Alexander et al. (U.S. Pat. Nos. 4,952,747; 4,952,748; 4,952,749; 4,982,049) have disclosed methods of removing some fractions of diamondoids from gas streams, the adamantane fraction of diamondoids in particular produced with the natural gas cannot be adequately absorbed by the methods disclosed in the Alexander patents for diamondoid removal (such as contacting the gas stream with a liquid solvent in which diamondoids are partially soluble, by injecting the solvent into producing wellheads and flowlines and subsequently removing the diamondoids by separating the gas from the diamondoid-laden solvent). Although diamondoid content is reduced, these methods do not remove a sufficient portion of the diamondoids to allow satisfactory operation of equipment without the concern of diamondoids plugging downstream equipment. In fact, additional processes such as silica gel absorbents as described in U.S. Pat. No. 4,952,748 may be required for further diamondoid removal to satisfactory levels.

With the current methods, a sufficient amount of diamondoids may be removed only if an extremely large amount of liquid solvent is mixed with the diamondoid-laden gas. Therefore, problems associated with residual amounts of the light diamondoids still remain and can occur when using the current methods in several instances such as the following: 1) diamondoid amounts absorbed by downstream glycol dehydration solvent (e.g. 0.06 lb/gal of glycol) would quickly load the glycol system charcoal filters. Frequent (weekly) filter change-out would be necessary to maintain the capability of removing diamondoids as well as other normal glycol degradation products in order to prevent glycol fouling and foaming problems; 2) flash gas recompression equipment, which returns low pressure gas from the glycol dehydration regeneration systems to the main gas flow would be handling gas streams with significant (up to 1500 lb/MSCF) diamondoid concentrations. Upon compression and cooling, diamondoids in this flash gas would precipitate and likely plug compressor discharge coolers and inlet scrubber mist extractors; and 3) diamondoids remaining in the dehydrated gas may precipitate in the produced gas pipeline; thereby potentially causing scaling and plugging problems. Therefore, there remains a need for a diamondoid removal process that can remove a sufficient amount of diamondoids from the natural gas, such that equipment problems caused by residual amounts of diamondoids are reduced, without the use of unusually large amounts of solvent.

SUMMARY OF THE INVENTION

The present invention provides a method for removal of diamondoid compounds from a natural gas stream by using a liquid solvent to absorb the diamondoids. This method of removing the diamondoid compounds from the natural gas can be implemented by contacting the diamondoid laden natural gas with a lean (diamondoid free) liquid solvent in a counter-current fashion such that the lean liquid initially contacts the leanest diamondoid gas (at the top of the tower) and then the liquid flows down the tower countercurrently through the diamondoid gas flow while progressively absorbing diamondoids from the richer diamondoid gas which is flowing up from the lower sections of the tower. This method can be implemented by initially separating liquid and natural gas from a wellhead into separate phases before contacting the natural gas in the liquid solvent absorber tower. This initial separation removes some diamondoids from the natural gas. The gas then flows to the absorber tower where more diamondoids are removed. The now diamondoid lean qas is separated from the now rich liquid solvent by the absorber tower itself. This partially saturated liquid solvent can then be injected into the wellhead flowline at a point before the initial separation of the liquid and natural gas such that it can mix with the diamondoid-laden gas and thereby absorb more diamondoids. This reduces diamondoid concentration in the natural gas flowing into the aforementioned contactor thereby enhancing efficiency of the process. In the implementation of this invention, a multi-staged trayed solvent contractor tower can be used to facilitate the actual contacting of the liquid solvent with the natural gas and the absorption of the diamondoids into the liquid solvent. Trayed towers and other similar devices bring about contact between the lean liquid solvent and diamondoid rich gas. The contact between liquid solvent and the gas causes the molecular mass transfer of the diamondoids to occur such that the diamondoid content of the gas is decreased and the diamondoid content of the liquid is conversely increased.

The method of this invention does not completely remove all of the diamondoids from the natural gas; however, this method will remove a sufficient amount of diamondoids from the natural gas stream such that the aforementioned problems would be manageable. The trace amounts of precipitating diamondoids in the natural gas and producing gas streams will be low enough that their accumulation will be inconsequential to the operation of the equipment

DETAILED DESCRIPTION OF THE INVENTION

Figure 1:
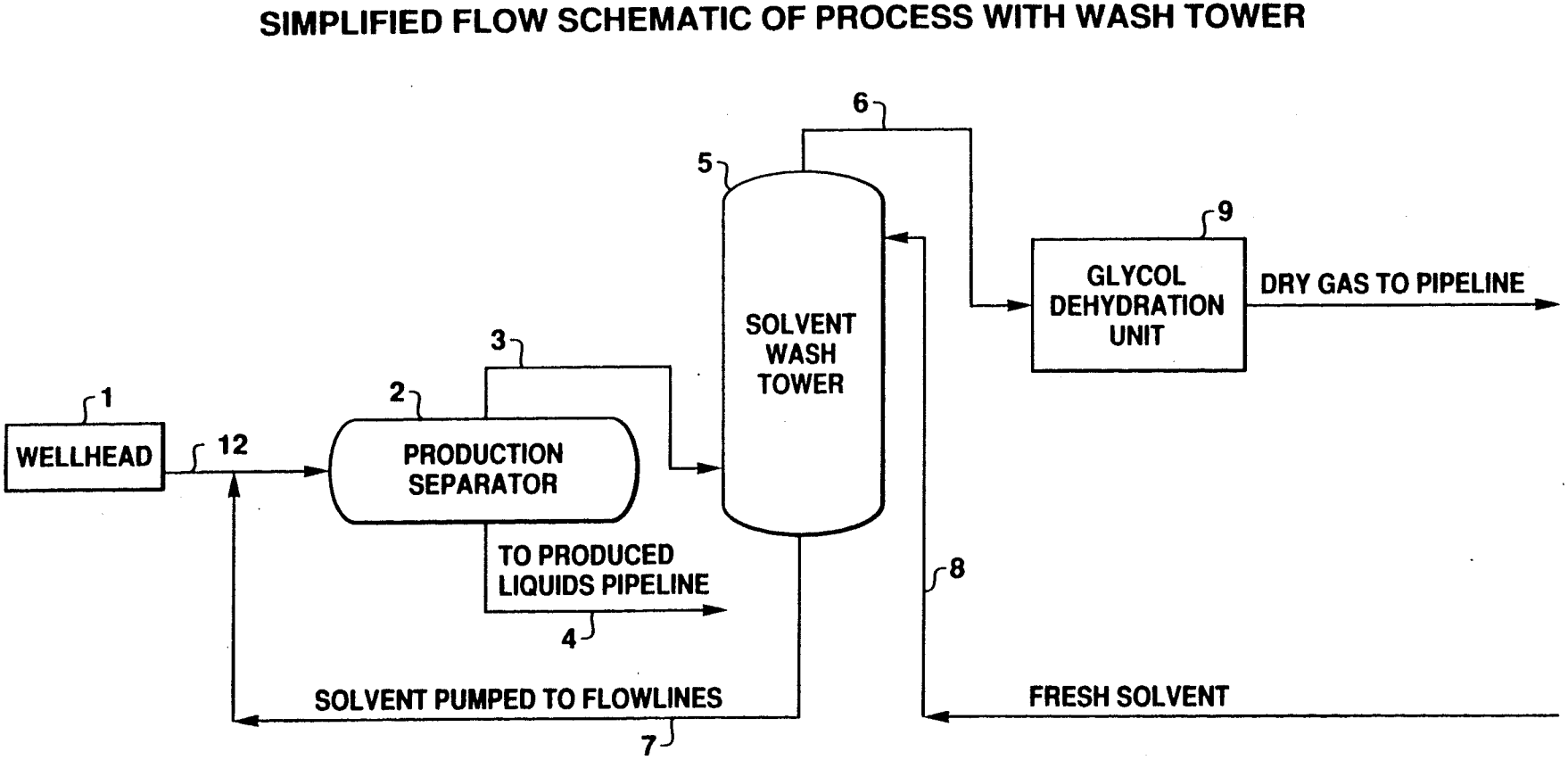
FIG. 1. Simplified flow schematic of the present invention using a solvent wash tower.
Figures 2A, 2B:
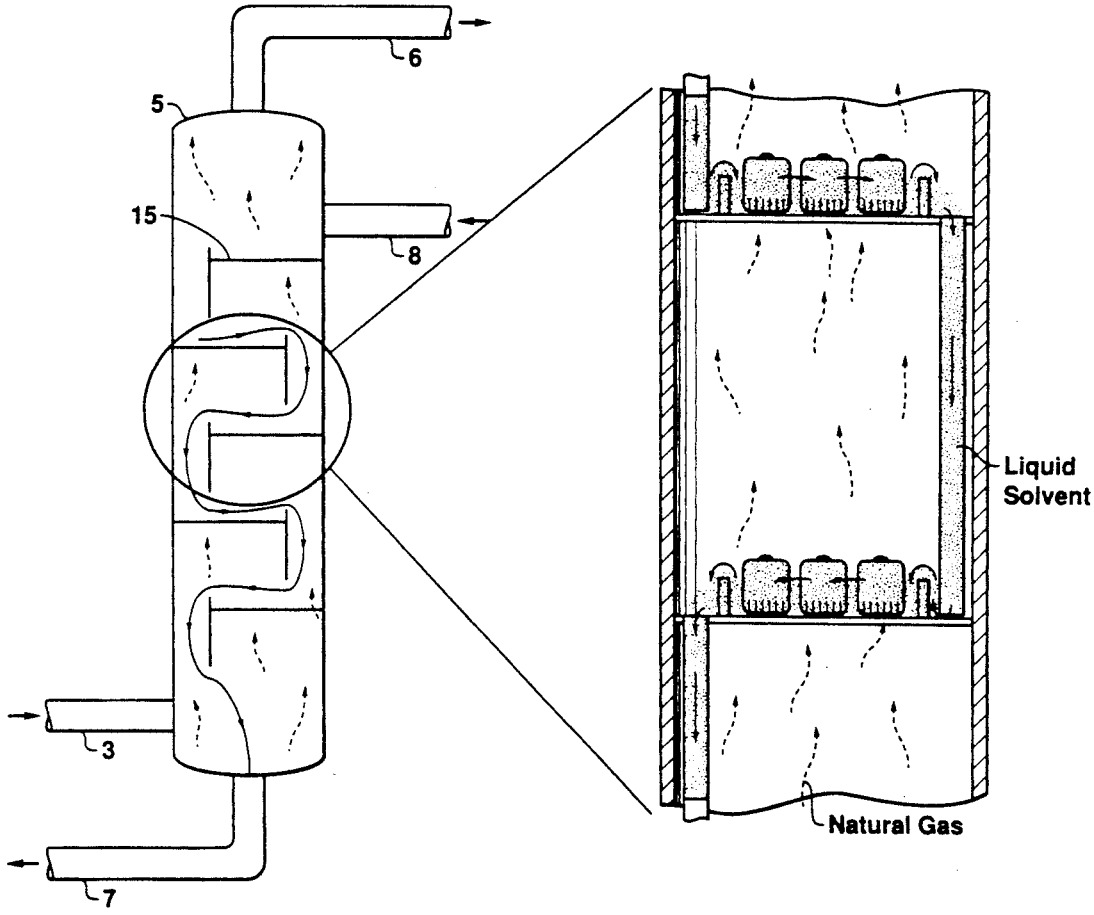
FIG. 2A. Cross-section of Solvent Contacting Tower.
FIG. 2B. Detail of Gas and Liquid Contacting Tray in Wash Tower.

FIG. 1 refers to a simplified flow schematic of the preferred embodiment of this invention for removing diamondoid compounds from natural gas. Diamondoid rich gas along with liquids from the reservoir formation at the wellhead 1 are mixed with a partially saturated liquid solvent at a point 12 before the gas enters the separator 2. At this stage the liquid solvent absorbs some of the diamondoids from the natural gas. The production separator 2 separates the natural gas from the liquid and discharges them through separate lines 3 and 4. The separation of the natural gas from the liquid removes the diamondoids absorbed thus far from the natural gas. The discharged natural gas then enters the solvent contactor tower 5. The contactor can have multi-staged trays, as shown in FIGS. 2A and 2B; however, other similar devices such as packed towers can perform the same functions as the contactor tower. FIG. 2B gives an example of typical contactor mixing trays. The operation of this contactor tower is already known to those skilled in the art.

In the preferred embodiment, diamondoid rich natural gas enters the tower 5 at a point near the bottom of the tower from line 3 and flows upward. A liquid solvent, such as diesel, enters the tower near the top from line 8 and flows downward. The tower FIG. 2A facilitates stepwise contact of liquid and gas in a counter current cascaded fashion. On each tray 15 of the tower, for example, the gas and liquid are brought into intimate contact (mixed) and then separated. This stepwise contact occurs because of the opposite flow of the natural gas and the liquid solvent in the tower. The contact and mixing of the gas and liquid allows chemical equilibrium forces to cause the molecular mass transfer of diamondoids to occur such that the diamondoid content of the gas is decreased and the diamondoid content of the liquid is conversely increased.

In order to maintain the maximum chemical equilibrium force, the tower 5 orientation is such that the leanest diamondoid gas is initially contacted by the leanest diamondoid liquid (at the top of the tower) and the richest diamondoid gas is contacted by the richest diamondoid liquid (at the bottom of the tower). The gas becomes progressively leaner in diamondoids as it travels up the tower length due to the cumulative absorption of diamondoids from the gas at each tray. Conversely, the liquid becomes progressively richer in diamondoids as it travels down the tower length due to the cumulative absorption of diamondoids into the liquid at each tray.

The diamondoid lean natural gas is discharged from the contactor tower 5, and flows through line 6 to other processing equipment such as a glycol dehydration unit 9. The glycol dehydration unit 9 removes water from the gas before pipeline transport.

Because diamondoids will quickly load up the charcoal filters in the glycol dehydration circulation system, this solvent wash contractor process must remove a substantial portion of the diamondoids (particularly adamantane fractions) from the natural gas stream before the gas reaches the glycol dehydration process. In order to achieve adequate diamondoid removal, prior art processes require large quantities of 100% fresh diamondoid solvent or additional downstream processes such as silica gel. However, the embodiment shown in FIG. 1 uses less fresh liquid solvent because this process allows the solvent from the contactor to be used a second time by pumping the solvent into the upstream end of each flowline at a point 12 before the gas enters the production separator 2. Mixing this solvent with the wellhead gas can remove some diamondoids from the gas and can prevent diamond precipitation problems at the wellhead facilities immediately downstream of the wellhead. The use of the absorber contactor with fresh solvent and reinjection of the contactor's discharged solvent not only increases the diamondoid removal but also reduces the solvent circulation rates from approximately 6.7 BL/MSCF to approximately 2.7 BBL/MSCF for the present invention as shown in Table 1.

As stated above one advantage of the present invention is that a larger percentage of diamondoids can be removed from the natural gas, by using less liquid solvent. The cleaner natural gas decreases the likelihood of equipment failure due to diamondoid contamination, thereby decreasing the amount of equipment maintenance time. Comparisons between the present method of wellhead injection only (Case 1) and this invention (Case 2) with a tower and wellhead injection are shown in Table 1 below.

Figure 3:
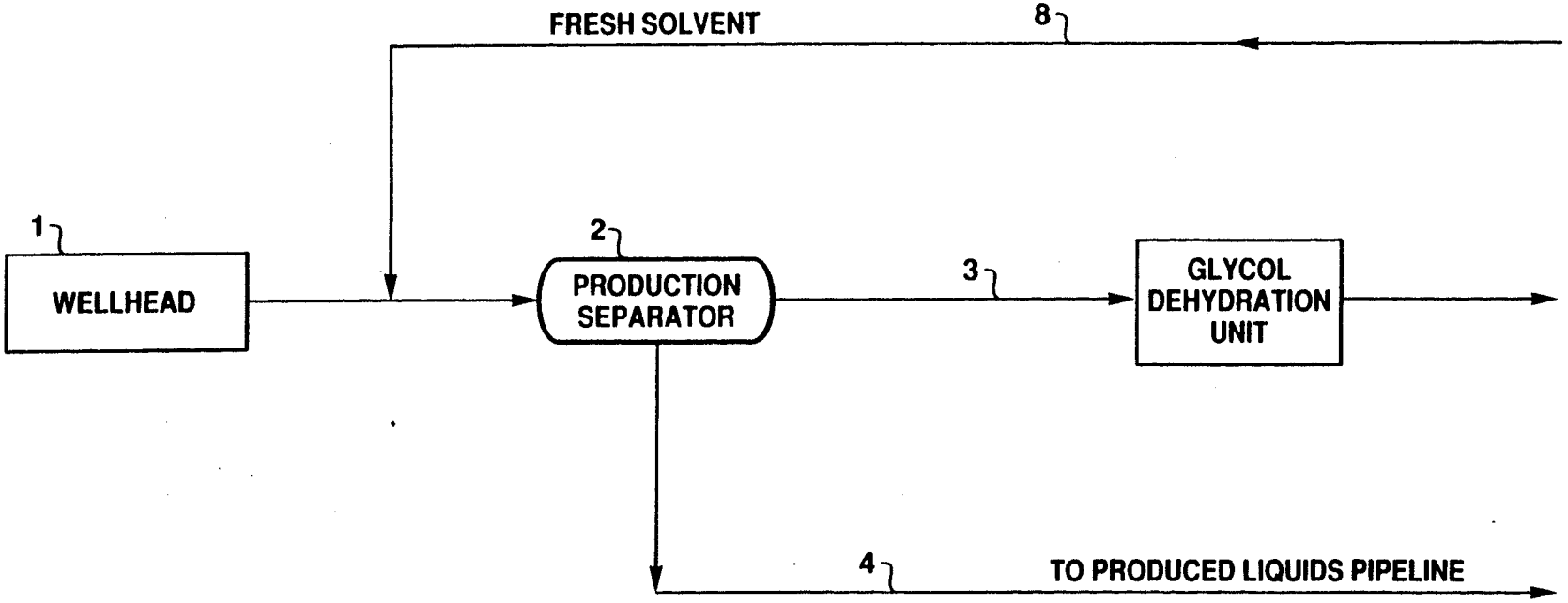
FIG. 3. Current process for removing diamondoids by mixing solvent with the natural gas containing diamondoids.

Case 1 is illustrated in FIG. 3. This case involves mixing the natural gas at the wellhead with a fresh diesel solvent, then separating the gas and the solvent. As stated previously, this method has a substantially higher diesel circulation rate than the present invention. This method removes some (approximately 95%) of the diamondoids from the gas. Also, as shown in Table 1, if the gas flowed through a glycol contactor 11 lb/hour of diamondoids would be absorbed by the glycol contactor.

Case 2 is the preferred embodiment of this invention and is illustrated in FIG. 1. As described previously, natural gas is initially mixed with a diesel solvent which has been recycled from the wash tower 5. This solvent contains some diamondoids from prior contact with natural gas in the wash tower. The solvent absorbs some of the diamondoids from the gas while in the flowline. The gas solvent mixture is then separated in the separator 2. The gas then enters the wash tower and contacts fresh diesel, where substantially all of the remaining diamondoids are removed from the gas. If the gas then flowed through a Glycol contactor only 1 lb/hour of diamondoids would be absorbed by the Glycol contactor. This number is substantially lower than simple flowline injection and uses a substantially lower amount of diesel.

While several embodiments and types of equipment have been described and illustrated, it will be understood that the invention is not limited thereto, since modifications may be made and will become apparent to those skilled in the art.

We claim that:

1. A process for removing diamondoid compounds from natural gas comprising the steps of:

a) providing a natural gas stream containing a concentration of diamondoid compounds;

b) mixing the natural gas with a liquid diamondoid absorbing solvent in a cascading manner where diamondoid rich natural gas contacts the lean solvent so that the solvent absorbs the diamondoids from the natural gas; and c) separating the diamondoid rich liquid solvent from the diamondoid lean natural gas.

2. A process of claim 1 wherein the mixing step (b) and the separating step (c) occur in a multi-staged solvent wash tower.

3. A process of claim 1 wherein the diamondoid absorbing solvent is comprised of diesel fluid.

4. A process for removing diamondoid compounds from a natural gas stream during natural gas processing comprising the steps of:

a) providing a natural gas stream containing a concentration of diamondoid compounds;

b) separating any liquid mixed with the natural gas so that the liquid and natural gas and liquid components are processed separately;

c) mixing the natural gas with a liquid diamondoid absorbing solvent in a cascading manner where diamondoid rich natural gas contacts the diamondoid lean solvent so that the solvent absorbs diamondoids from the natural gas; and d) separating the diamondoid rich liquid solvent from the diamondoid lean natural gas.

5. A process of claim 4 wherein the mixing step (c) and separating step (d) occur in a multi-staged solvent wash tower.

6. A process of claim 4 wherein the diamondoid absorbing solvent is comprised of diesel fluid.

7. A process of claim 4 further comprising the step of recycling the partially saturated solvent of step (d) back into the flowline at a point in the flowline before step (b) so that the liquid solvent absorbs some of the diamondoids.

8. A process for removing diamondoid compounds from a natural gas stream comprising the steps of:

a) providing a natural gas stream in a flowline;

b) mixing a liquid solvent that is partially saturated with diamondoids with the natural gas in the flowline so that the liquid solvent absorbs some of the diamondoids out of the gas;

c) separating the liquid solvent from the gas;

d) mixing the natural gas with a fresh liquid diamondoid absorbing solvent in a cascading manner where diamondoid rich gas contacts diamondoid lean solvent so that the solvent absorbs diamondoids from the natural gas; and e) separating the solvent from the diamondoid lean natural gas.

9. A process of claim s, wherein the mixing step (d) and the separating step (e) occur in a multi-staged solvent wash tower.

10. A process of claim 8, wherein the diamondoid absorbing solvent is comprised of diesel fluid.

11. A process of claim 8 further comprising the step of recycling the partially saturated solvent of step (e) back into the flowline at a point in the flowline such that the mixing step (b) will occur.

* * * * *